United States Patent [19]

Calabrese et al.

[11] Patent Number: 5,054,475

[45] Date of Patent: Oct. 8, 1991

[54] EMERGENCY MEDICAL COLLAR, COLLAR/STABILIZER, COLLAR/STABILIZER/HEAD IMMOBILIZER

[75] Inventors: Anthony Calabrese, Philadelphia; Sandy Scialli, Richboro, both of Pa.

[73] Assignee: Charles Greiner and Company, Inc., Westville, N.J.

[21] Appl. No.: 171,245

[22] Filed: Mar. 18, 1988

Related U.S. Application Data

[63] Continuation-in-part of Ser. No. 121,490, Nov. 17, 1987, abandoned.

[51] Int. Cl.⁵ .................... A61F 5/00; A61F 5/04
[52] U.S. Cl. .................... 128/75; 128/76 R; 128/78; 128/87 B
[58] Field of Search ............. 128/75, 76 R, 77, 78, 128/87 B, 846, 869, 870; 2/173, 206

[56] References Cited

U.S. PATENT DOCUMENTS

| | | | |
|---|---|---|---|
| D. 95,729 | 2/1935 | Brown | D24/64 |
| D. 209,116 | 10/1967 | Treutelaar | D24/64 |
| D. 213,742 | 4/1969 | Bond | 24/64 |
| D. 228,964 | 10/1973 | Sarnoff | D24/64 |
| D. 278,747 | 5/1985 | Peach, Jr. | D24/64 |
| D. 289,085 | 3/1987 | Nesbitt | D24/64 |
| 106,091 | 8/1870 | Stowe | 128/89 A |
| 1,301,276 | 4/1919 | Kroetz | 128/78 |
| 2,151,458 | 3/1939 | Allen | 128/87 R |
| 2,272,959 | 2/1942 | Van Wormer | 2/173 |
| 2,325,300 | 7/1943 | Bisnoff | 128/87 R |
| 2,556,793 | 6/1951 | Brown | 128/164 |
| 2,672,146 | 3/1954 | Touson | 128/303 R |
| 2,692,595 | 10/1954 | Blair, Jr. | 128/87 B |
| 2,740,399 | 4/1956 | Judovich | 128/75 |
| 2,818,063 | 12/1957 | Smith et al. | 128/87 B |
| 2,827,896 | 3/1958 | Ward | 128/75 |
| 3,042,027 | 7/1962 | Monfardini | 128/75 |
| 3,156,239 | 11/1964 | Uribe | 128/75 |
| 3,189,917 | 2/1962 | Sims | 128/87 R X |
| 3,220,406 | 11/1965 | Connelly . | |
| 3,285,243 | 11/1966 | Yellin | 128/75 |
| 3,306,284 | 2/1967 | McKinley | 128/75 |
| 3,313,297 | 4/1967 | Applegate et al. | 128/75 |
| 3,504,667 | 4/1970 | McFarlane | 128/75 |
| 3,540,439 | 11/1970 | Gaylord | 128/75 |
| 3,724,453 | 4/1973 | Dixon et al. | 128/87 R |
| 3,756,226 | 9/1973 | Calabrese et al. | 128/75 |
| 3,759,256 | 9/1973 | O'Malley | 128/89 A |
| 3,779,549 | 12/1973 | MacNeil | 273/1 B |
| 3,818,509 | 6/1974 | Romo et al. | 2/421 |
| 3,819,796 | 6/1974 | Webster | 264/321 |

(List continued on next page.)

FOREIGN PATENT DOCUMENTS 2165157A  4/1986  United Kingdom .

OTHER PUBLICATIONS

*Orthopaedic Appliances Atlas*, p. 240, FIGS. 296, 297, 1952.

*Primary Examiner*—Richard J. Apley
*Assistant Examiner*—Karen G. Horowitz
*Attorney, Agent, or Firm*—Panitch Schwarze Jacobs & Nadel

[57] ABSTRACT

The present invention is directed to a head immobilizer used with a cervical collar. The cervical collar comprises a front and rear half, each half being U-shaped, and a reinforcing member affixed to each half. A head immobilizer generally includes a head rest which is T-shaped and which has a stem and two arms. Each arm has a distal end. The stem releasably engages the reinforcing member affixed to the rear half of the collar. A fastening device is affixed to the distal end of each arm. A mask has an opening therethrough and overlaps, in part, the front half of the collar. A mating device is affixed to the mask and engages the fastening device. A securing device is affixed to the mask and engages the fastening device. Whereby, a victim's head is immobilized between the head rest, mask, and collar, when the fastening device is connected with the mating device and the securing device.

33 Claims, 18 Drawing Sheets

U.S. PATENT DOCUMENTS

| | | | |
|---|---|---|---|
| 3,916,885 | 11/1975 | Gaylord, Jr. | 128/75 |
| 3,957,040 | 5/1976 | Calabrese | 128/75 |
| 4,141,368 | 2/1979 | Meyer | 128/87 B |
| 4,143,654 | 3/1979 | Sherman | 128/87 R |
| 4,161,946 | 7/1979 | Zuesse | 128/75 |
| 4,190,054 | 2/1980 | Brennan | 128/402 |
| 4,202,327 | 5/1980 | Glancy | 128/78 |
| 4,207,881 | 6/1980 | Richter | 128/89 A |
| 4,211,218 | 7/1980 | Kendrick | 128/87 R |
| 4,219,193 | 8/1980 | Newman | 272/94 |
| 4,383,523 | 5/1983 | Schurman | 128/75 |
| 4,422,454 | 12/1983 | English | |
| 4,502,471 | 3/1985 | Owens | 128/75 |
| 4,515,153 | 5/1985 | Calabrese | 128/87 |
| 4,538,597 | 9/1985 | Lerman | 128/75 |
| 4,562,833 | 1/1986 | Pujals, Jr. | 128/75 |
| 4,582,051 | 4/1986 | Greene et al. | 128/76 R |
| 4,589,407 | 5/1986 | Koledin et al. | 128/87 R |
| 4,593,788 | 6/1986 | Miller | 182/3 |
| 4,594,999 | 6/1986 | Nesbitt | 128/87 |
| 4,620,530 | 11/1986 | Lanier et al. | 128/75 |
| 4,628,913 | 12/1986 | Lerman | 128/78 |
| 4,643,174 | 2/1987 | Horiuchi | 128/76 R |
| 4,650,182 | 3/1987 | Ross | 272/95 |
| 4,657,003 | 4/1987 | Wirtz | 128/133 |
| 4,665,908 | 5/1987 | Calkin | 128/134 |
| 4,677,969 | 7/1987 | Calabrese | 128/75 |
| 4,700,691 | 10/1987 | Toni et al. | 128/869 |

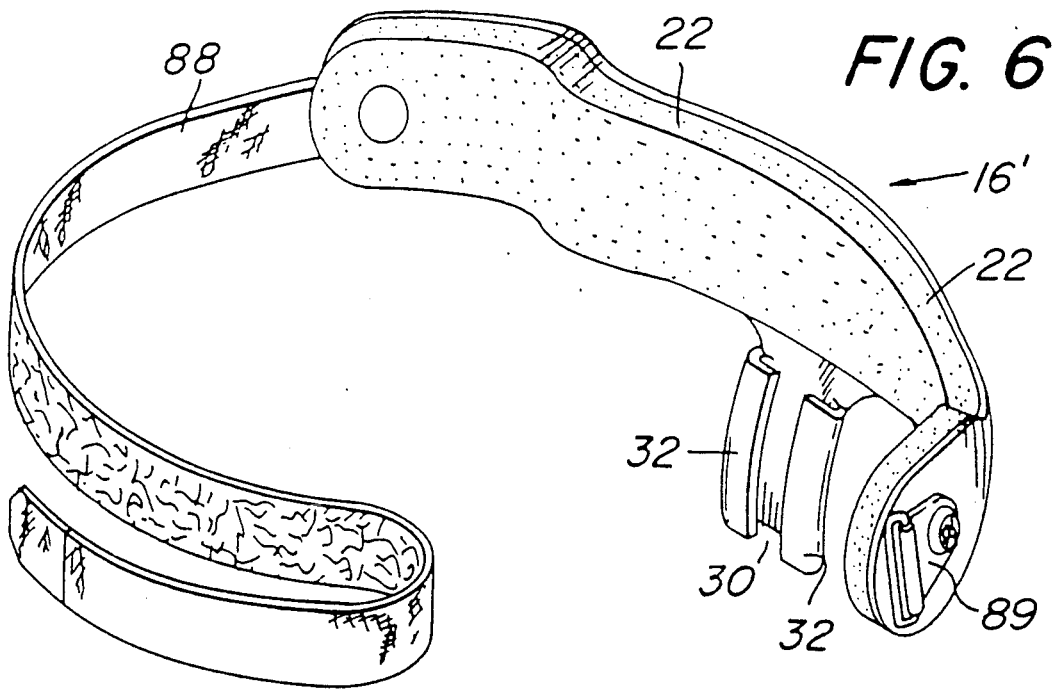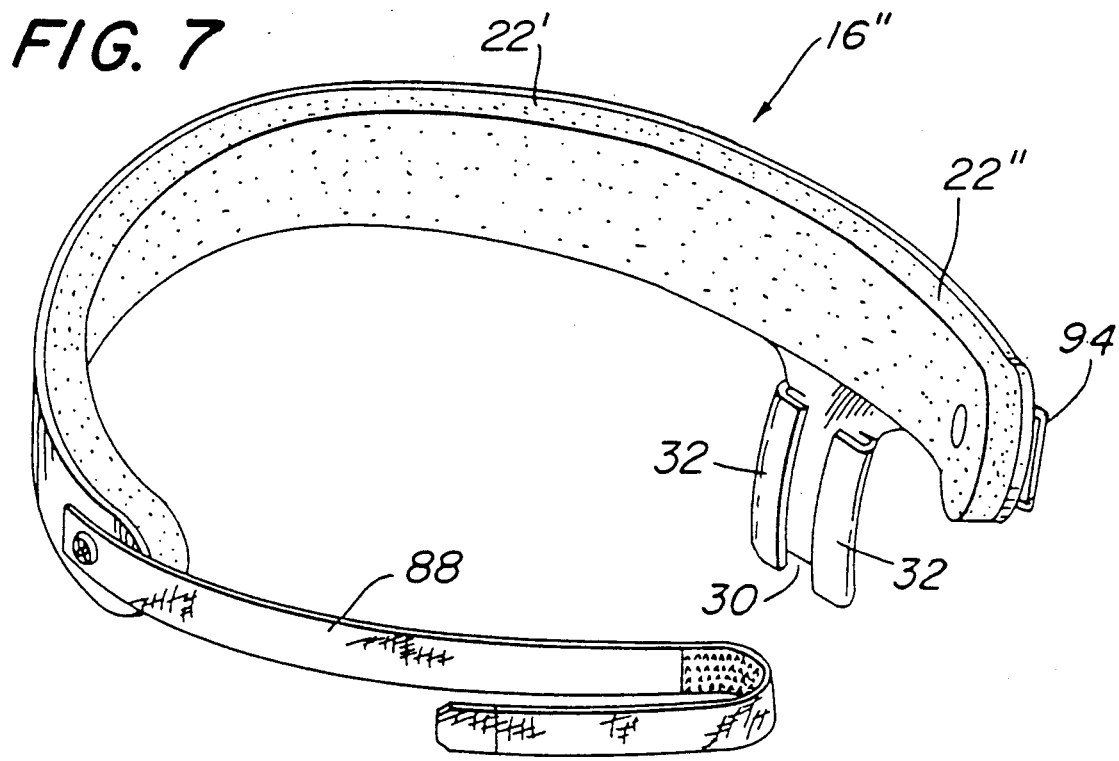

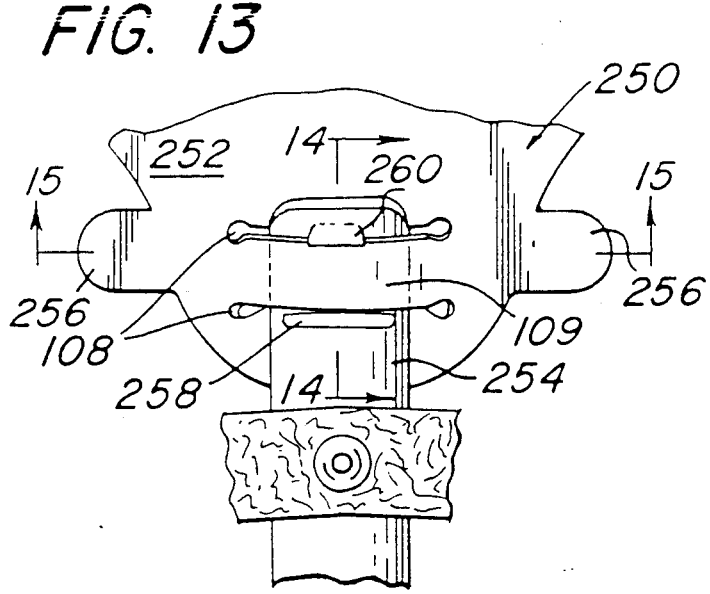
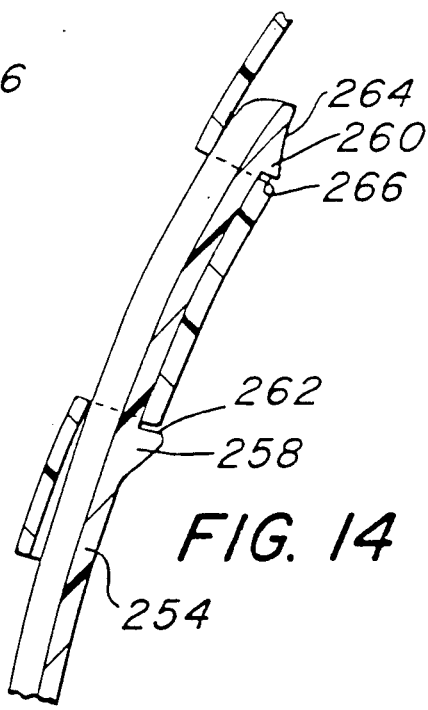
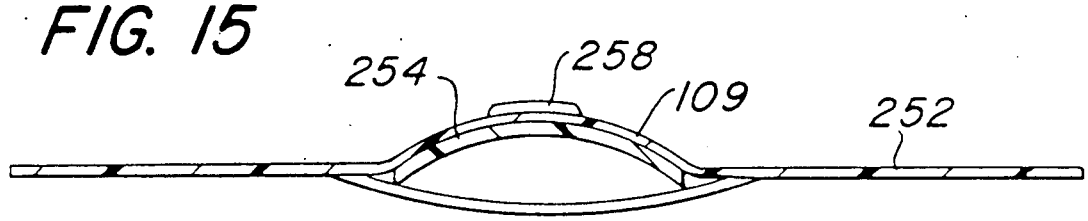
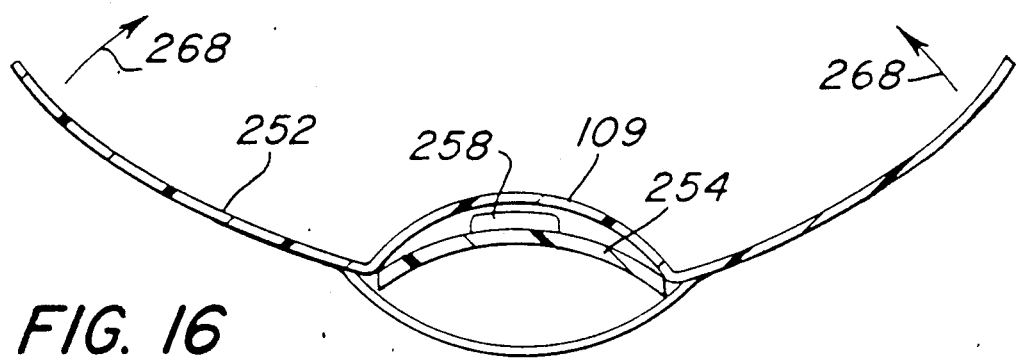

5,054,475

EMERGENCY MEDICAL COLLAR, COLLAR/STABILIZER, COLLAR/STABILIZER/HEAD IMMOBILIZER

RELATED APPLICATION

The instant application is a continuation-in-part of co-pending U.S. patent application Ser. No. 121,490 filed Nov. 17, 1987, and now abandoned.

REFERENCE TO RELATED APPLICATIONS

This application is related to U.S. patent application Ser. No. 07/125,730 now U.S. Pat. No. 4,886,052, a continuation-in-part of Ser. No. 07/70,992, filed July 8, 1987, now abandoned, which is a continuation-in-part of Ser. No. 07/41,898, filed Apr. 23, 1987, and to U.S. Pat. Nos. 4,502,471 and 4,677,969.

SCOPE OF THE INVENTION

The present invention is directed to a head immobilizer which is used in combination with a cervical collar or a cervical collar/stabilizer combination.

BACKGROUND OF THE INVENTION

Head immobilization is necessary when an accident victim has suffered trauma to his/her head, neck, and/or spine. Various cervical collars and cervical collar/stabilizer combinations are disclosed in the instant assignee's prior U.S. patents, U.S. Pat. Nos. 3,756,226; 4,502,471; 4,515,153; and 4,677,969. Assignee's U.S. Pat. No. 3,957,040 discloses a head immobilization device, but it is not readily usable by emergency medical teams.

U.S. Pat. No. 4,143,654 illustrates, in FIG. 3, the use of a spine board system in combination with a cervical collar. The spine board system comprises a board having a vest at its lower end and two pairs of notches at its upper end. The notches are engaged by head and chin straps which fix the wearer's head against the board. The spine board is not connected to the cervical collar.

U.S Pat. No. 4,161,946 illustrates, in FIGS. 6-8, an inflatable head support. The support comprises a bladder having a lower portion which surrounds the neck and an upper portion which surround a substantial portion of the head,.but excludes the face of the wearer. The support also includes a strap which is fastened to the upper portion and secures the wearer's head within the upper portion.

U.S. Pat. No. 4,657,003 illustrates, in FIGS. 12-14, a collar and head immobilizer, and, in FIGS. 15-17, a head and neck immobilizer which surround the neck, a substantial portion of the head and a part of the upper torso. Both embodiments are constructed in such a way that they are made rigid by evacuation. The first embodiment, the collar and head immobilizer, comprises a rectangular center portion which wraps around the back and sides of the wearer's head and end tabs which meet under the wearer's chin. The second embodiment, the head and neck immobilizer, comprises a one piece device which straps around the wearer's neck, a substantial portion of the wearer's head, and upper torso.

U.S. Pat. Nos. 4,677,969; 4,582,051; 4,515,153; and 4,502,471 each disclose a cervical collar and stabilizer combination. U.S. Pat. Nos. 4,141,368 and 3,957,040 each disclose head immobilizer and stabilizer combinations. U.S. Pat. Nos. 4,538,597 and Design 279,747 are directed to cervical collars. U.S. Pat. No. 1,301,276 discloses an open faced mask in FIG. 3.

SUMMARY OF THE INVENTION

The present invention is directed to a head immobilizer used with a cervical collar. The cervical collar has a member affixed thereto which receives the head immobilizer. The head immobilizer includes a head rest for supporting the rear of the victims head, a mask and a connecting device. The head rest releasably engages the member affixed to the collar, thereby rigidly securing the head rest to the collar in a fixed relation. The mask has an opening therethrough, and one portion of the mask overlaps the victims forehead while another portion of the mask overlaps the collar. The connecting device joins the mask to the head rest such that a victim's head is immobilized between the head rest, mask, and collar.

DESCRIPTION OF THE DRAWINGS

For the purpose of illustrating the invention, there is shown in the drawings a form which is presently preferred; it being understood, however, that this invention is not limited to the precise arrangements and instrumentalities shown.

FIG. 6 is an isometric view of a first alternate embodiment of the present invention.

FIG. 7 is an isometric view of a second alternate embodiment of the present invention.

FIG. 13 is an elevational view of an alternate embodiment of the sleeve attachment device illustrated in FIGS. 10-12.

FIG. 14 is a sectional view taken along lines 14—14 of FIG. 13.

FIG. 15 is a sectional view taken along lines 15—15 of FIG. 13.

FIG. 16 is a sectional view similar to that shown in FIG. 15 which illustrates the release movement of the embodiment of FIGS. 13-16.

DETAILED DESCRIPTION OF THE INVENTION

Figure 1:
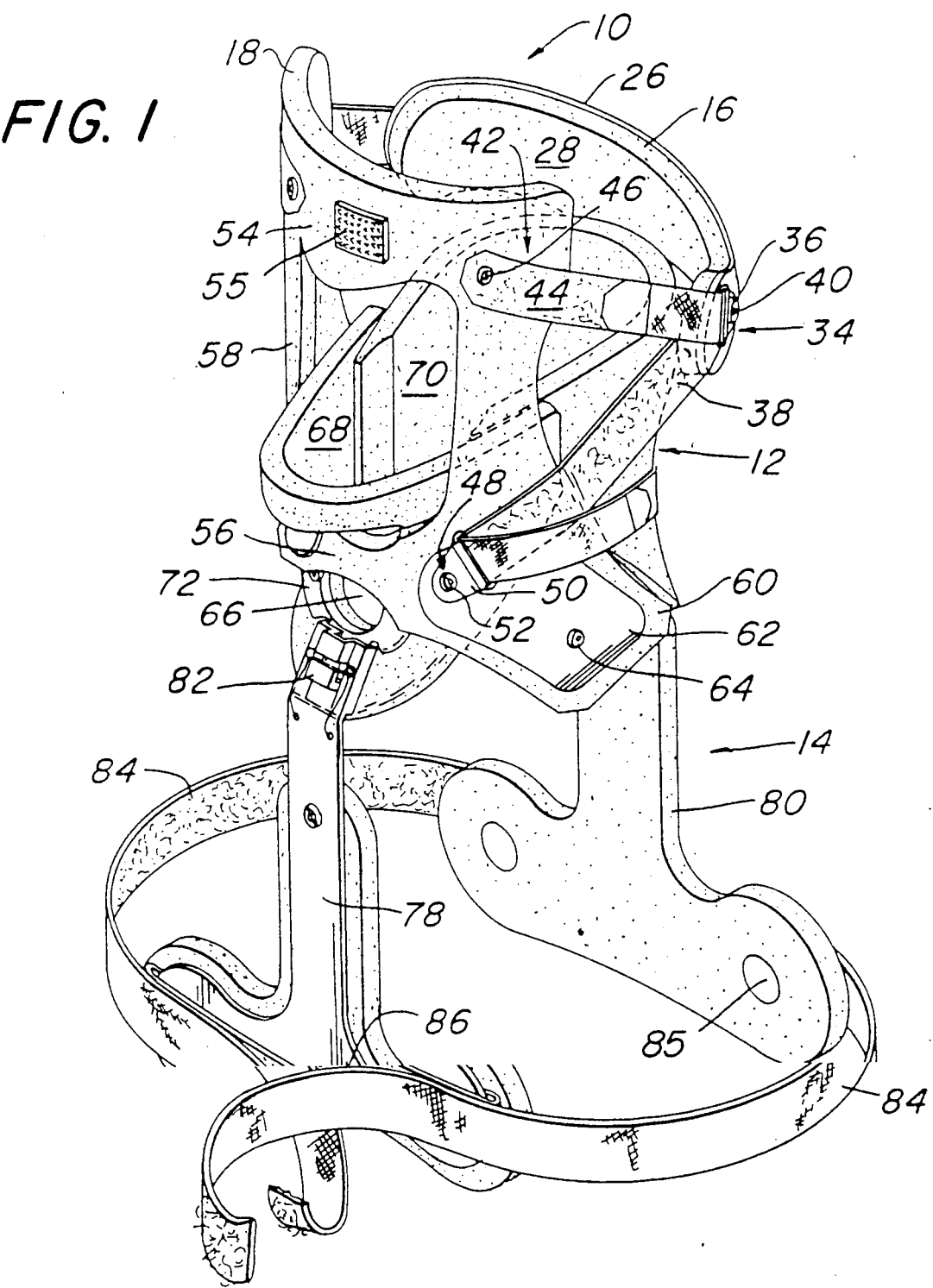
FIG. 1 is an isometric view of the preferred embodiment of the present invention, illustrated in combination with a cervical collar and stabilizer.

Referring to the drawings, there is illustrated in FIG. 1 a preferred embodiment of the head immobilizer 10 in combination with a cervical collar 12 and stabilizer 14. U.S. Pat. Nos. 3,756,226; 4,502,471; 4,515,153; 4,677,969; U.S. patent application Ser. No. 41,898 filed Apr. 23, 1987, entitled "Emergency Medical Cervical Collar" by Anthony Calabrese; and U.S. patent application Ser. No. 70,922 filed July 8, 1987, entitled "Emergency Medical Cervical Collar" by Anthony Calabrese are incorporated herein by reference as they are related to cervical collars and cervical collar/stabilizer combinations such as those generally described hereinafter. U.S. Pat. No. 3,957,040 is also incorporated here reference and is directed to a cervical brace.

Cervical collar 12 may be any of the collars described in any of the incorporated references listed above which are modified as follows. Rear collar half 70, referring to FIG. 3 herein, is provided with a horizontally disposed VELCRO® "loop" strap 74 which is secured to the collar half 70 by a rivet 76 or other fastener. The upper portion of reinforcing member 72 must be detached from the collar portion it overlaps, so that a head rest 16 can be slid over or attached to it, as will be described in greater detail below. A tracheotomy opening 66 is preferably provided in front half 68. The chin support portion of front half 68 is preferably flexible so that it may be folded away from the chin so as to permit vomiting and movement of the jaw.

Stabilizer 14 may be any of the stabilizers described in any of the incorporated references listed above which are modified as follows. Front stabilizer half 78 is provided with a VELCRO® "hook" strap 86 which is engaged by straps 84 fastened to rear stabilizer half 80 by fasteners 85, such as rivets. Connection device 82 can be any of those previously described in the references incorporated herein.

The head immobilizer 10 generally comprises a head rest 16, a mask 18, and a connecting device. The connecting device comprises a fastening device 34 affixed to the head rest 16, a mating device 42 affixed to the mask 18, and a securing device 48 affixed to mask 18. Immobilizer 10 may also be embodied in alternative forms illustrated in FIGS. 6 and 7 as will be discussed in greater detail after an explanation of the preferred embodiment, which follows.

Figure 3:
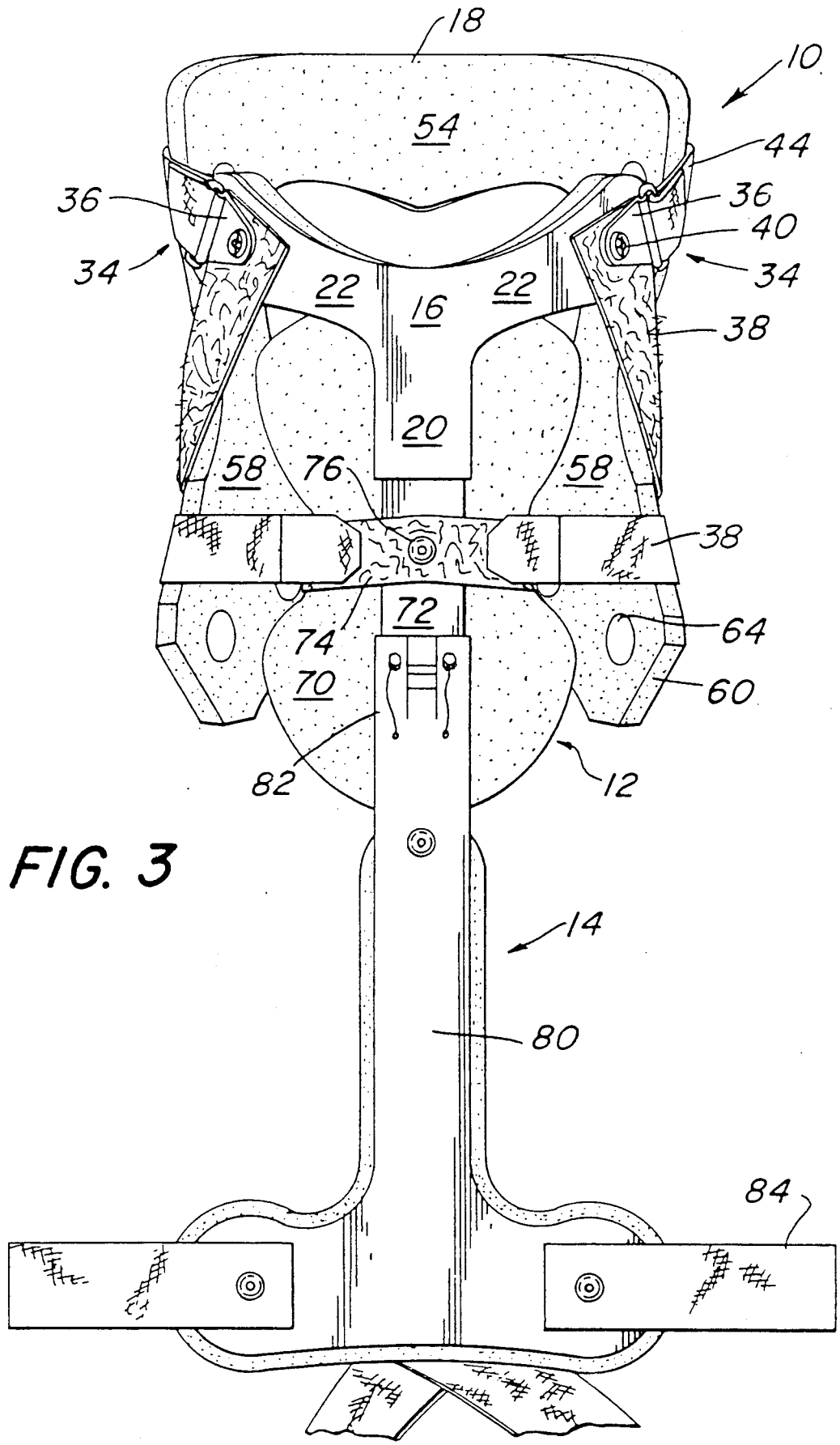
FIG. 3 is a rear elevational view of the embodiment of FIG. 1.

Head rest 16, see FIG. 3, is generally "T"-shaped and includes a stem 20 and two arms 22. The head rest 16 comprises a reinforcement member 26, made of a rigid material, such as plastic. Reinforcement member 26 provides rigid support for the back of the victim's head. A padding material 28 is affixed to the reinforcement member 26. Padding material 28 is a foam material which covers the inner surface of the arms of member 26. Padding material 28 may be secured to reinforcement member 26 in any well known manner. Stem 20 is shaped to form a channel 30 by folding over guides 32. See FIGS. 6 and 7. Channel 30 is sized for receipt of collar reinforcement member 72. Stem 20 slidably engages and mounts on reinforcement member 72 and is preferably secured thereon by friction. Alternatively, stem 20 may take on the form of connection device 82 mentioned above.

Figure 2:
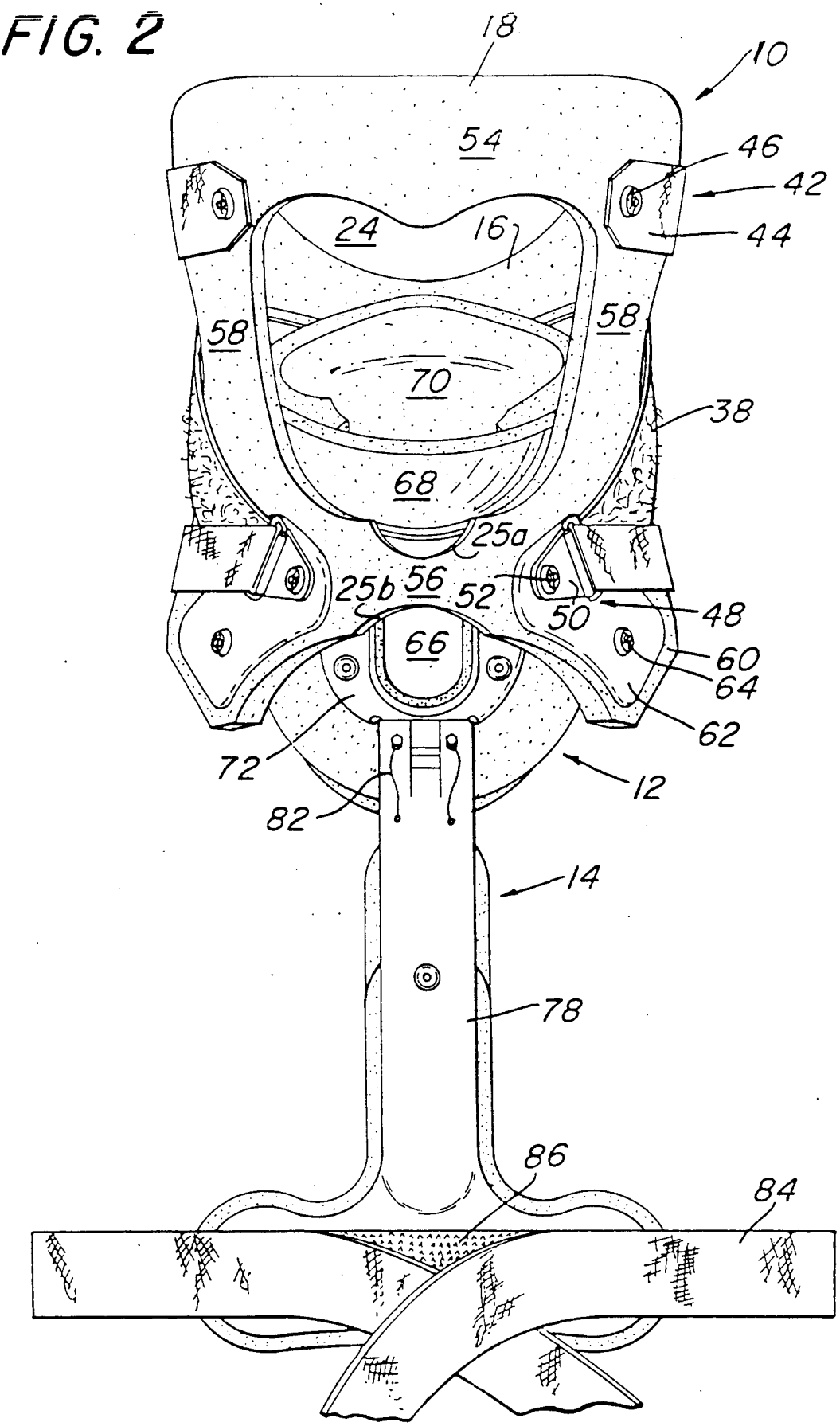
FIG. 2 is a front elevational view of the embodiment of FIG. 1.
Figure 4:
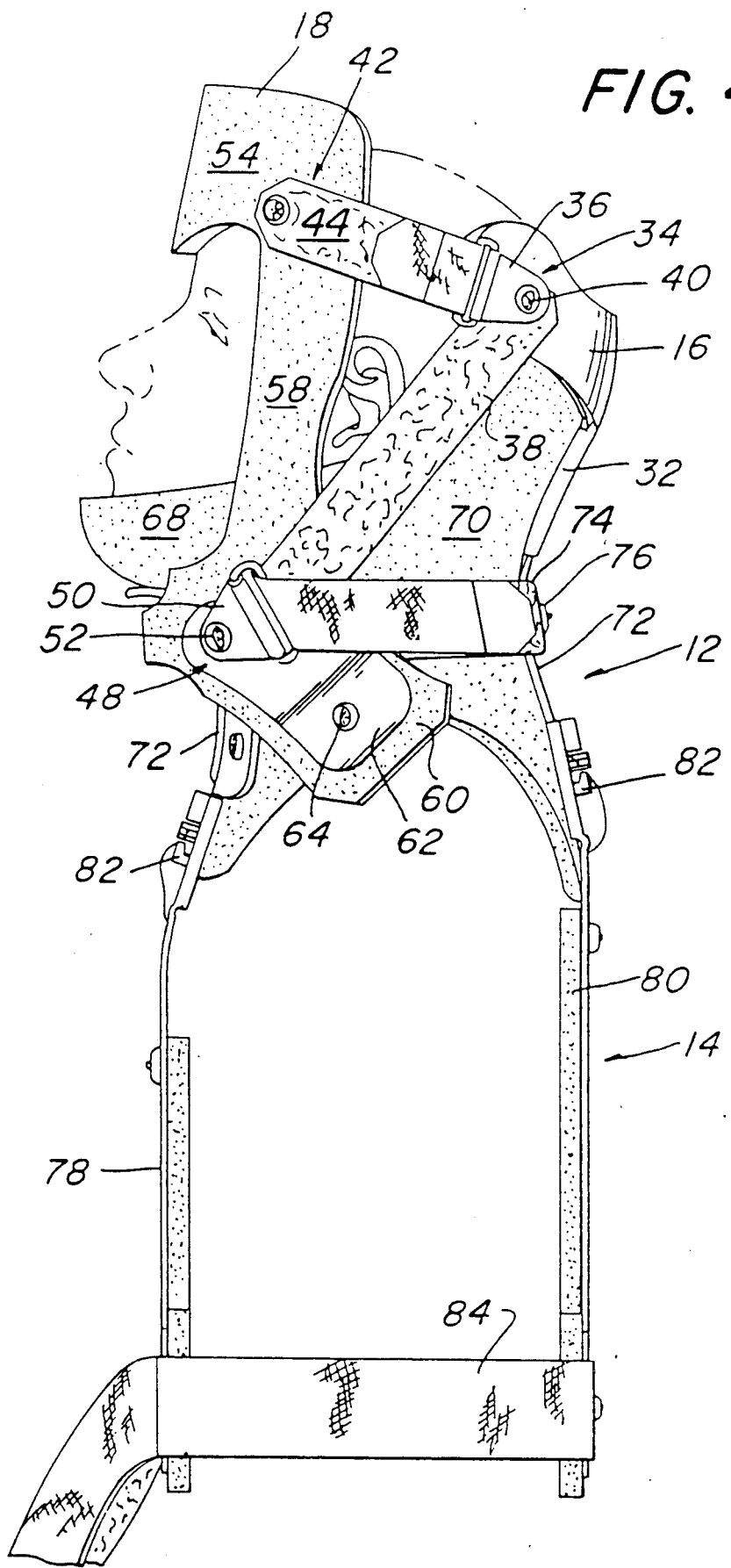
FIG. 4 is a side elevational view of the embodiment of FIG. 1 and illustrates a first head immobilizer strap configuration (hereinafter the "Z" strap embodiment).
Figure 5:
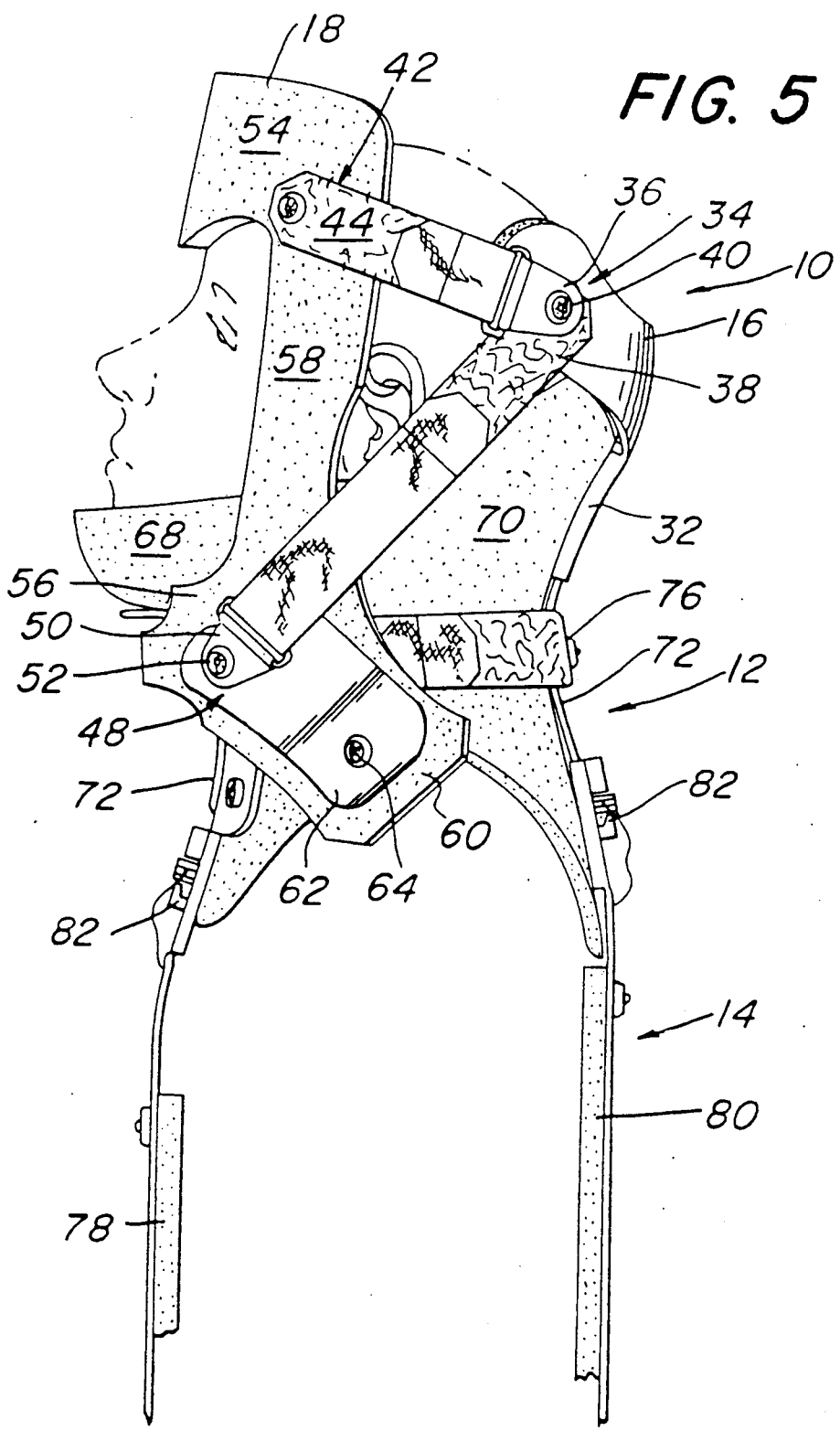
FIG. 5 is a side elevational view of the preferred embodiment of the present invention and illustrates a second head immobilizer strap configuration (hereinafter the "V" strap embodiment).

Mask 18 is preferably a generally rectangular piece of resilient foam material having an opening therethrough. See FIGS. 1 and 2. The opening is sized to permit exposure of the victim's face, but overlaps the victim's forehead. See FIGS. 4 and 5. The portion of mask 18 which overlaps the forehead is designated as upper mask portion 54. A lower mask portion 56, which fits below the victim's chin, overlaps the front half 68 of collar 12. The chin portion of front collar half 68 protrudes through opening, as illustrated in FIGS. 1, 4 and 5. An upper crescent shaped cutout 25a is preferably provided in the portion 56 to prevent mask 18 from buckling when it is placed over front half 68. A lower crescent shaped cutout 25b is preferably provided to allow access to tracheotomy opening 66. Upper and lower mask portions 54 and 56 are integrally joined together by lateral side members 58. In the lower corners of mask 18 are wings 60 which are integral with the mask 18 and which extend away from mask 18 at about a 45° angle. A reinforcement member 62 made of a rigid plastic material is preferably affixed to each wing 60 by fasteners 52 and 64, preferably rivets. Wing 60 and reinforcement member 62 spans the space between the victim's clavicle and the portion of the collar adjacent the jaw thereby impeding or preventing side-to-side (tilting) movement and forward movement of the victim's head.

Fastening device 34 is affixed to the distal ends of each arm 22 of headrest 16. See FIGS. 1, 3, 4 and 5. Fastening device 34 comprises a pivotable buckle 36 and a strap 38. A fastener 40, preferably a rivet, secures the fastening device 34 to arm 22. Strap 38, as all straps discussed hereinafter unless noted to the contrary, is made VELCRO® materials, in which a substantial portion of the strap is formed with "loops" and the terminal or free end of the strap comprises "hooks".

A mating device 42 is affixed generally to the upper corners of mask 18. See FIGS. 1, 4 and 5. Mating device 42 comprises a strap 44 which is affixed to mask 18 by fastener 46, such as a rivet.

A securing device 48 is affixed generally to the lower corners of mask 18, and comprises a pivotable buckle 50 which is preferably secured to reinforcement member 62 via fastener 52, such as a rivet. See FIGS. 1, 2, 4 and 5.

The interconnection of the fastening device 34, mating device 42 and securing device 48 may assume two alternate configurations as illustrated in FIG. 4 (the "Z" strap configuration) and FIG. 5 (the "V" strap configuration). Note that in both configurations, the victim's ear is accessible so that it may be inspected and blood, spinal fluid, or other foreign matter may be removed therefrom. In the "Z" strap configuration, mating device strap 44 is passed through fastening device buckle 36, pulled taut, and fastened back upon itself via use of the loops and hooks of the strap. Fastening device strap 38 is passed through securing device buckle 50, pulled taut, and the hook fasteners of strap 38 are secured upon loop strap 74 of rear collar half 70.

In the "V" strap configuration, mating device strap 44 is passed through fastening device buckle 36, pulled taut, and secured upon itself, as discussed above. Fastening device strap 38 is passed through securing device buckle 50, pulled taut, and fastened onto itself via the loop and hook fasteners.

In FIGS. 6 and 7, the alternate embodiments of the immobilizer 10 are illustrated. These alternate embodiments do not require the use of mask 18. Head rest 16', FIG. 6, is generally "T"-shaped and has arms 22 of equal length. Each arm preferably includes an arcuate section which permits the arm to pass above the ear and remain in contact with the head. A strap 88 bridges the gap between the two arms 22 and overlaps the victim's forehead. Strap 88 is affixed to a distal end of an arm 22, preferably by a rivet. The strap 88 is passed through a pivotable buckle 89 located on the distal of the other arm 22 and is secured to itself via the loop and hook fasteners of the strap. Preferably, a piece of horsehide (not shown) is affixed to the strap for contact with the victim's forehead. Second alternate head rest 16" includes one arm 22' which is substantially longer than the other arm 22'. Like head rest 16', this embodiment also includes a strap 88 and buckle 89 and is used in a like manner. The straps 88 and 89 of both alternate embodiments 16' and 16" may comprise an elastic portion which is connected between the arm's distal end and the VELCRO ® strap.

Figure 8:
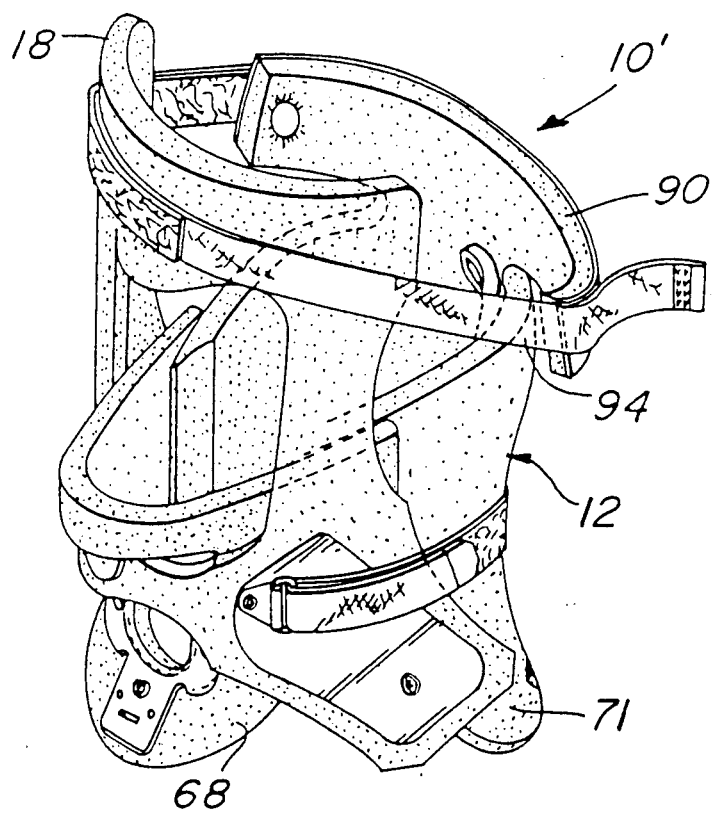
FIG. 8 is an isometric view of a third alternate embodiment of the present invention illustrated in combination with a cervical collar.

FIG. 8 illustrates a head immobilizer 10' in use with a cervical collar 12, but excluding the stabilizer 14. Compare with FIG. 1. The embodiment of FIG. 1 is preferred because it completely immobilizes the victim's head. If the stabilizer 14 is not used, the victim's head can tilt backward (i.e. hyperextend) and pivot on the seventh vertebra. The head immobilizer and collar reduces hyperextension, but the immobilizer and collar with the stabilizer can completely prevent hyperextension. The head immobilizer 10' is similar to those previously described, but differs, significantly, in that the head rest is integral with the rear collar half and a skirt 91 or lower portion of the rear collar half is enlarged, as discussed below.

Figure 9:
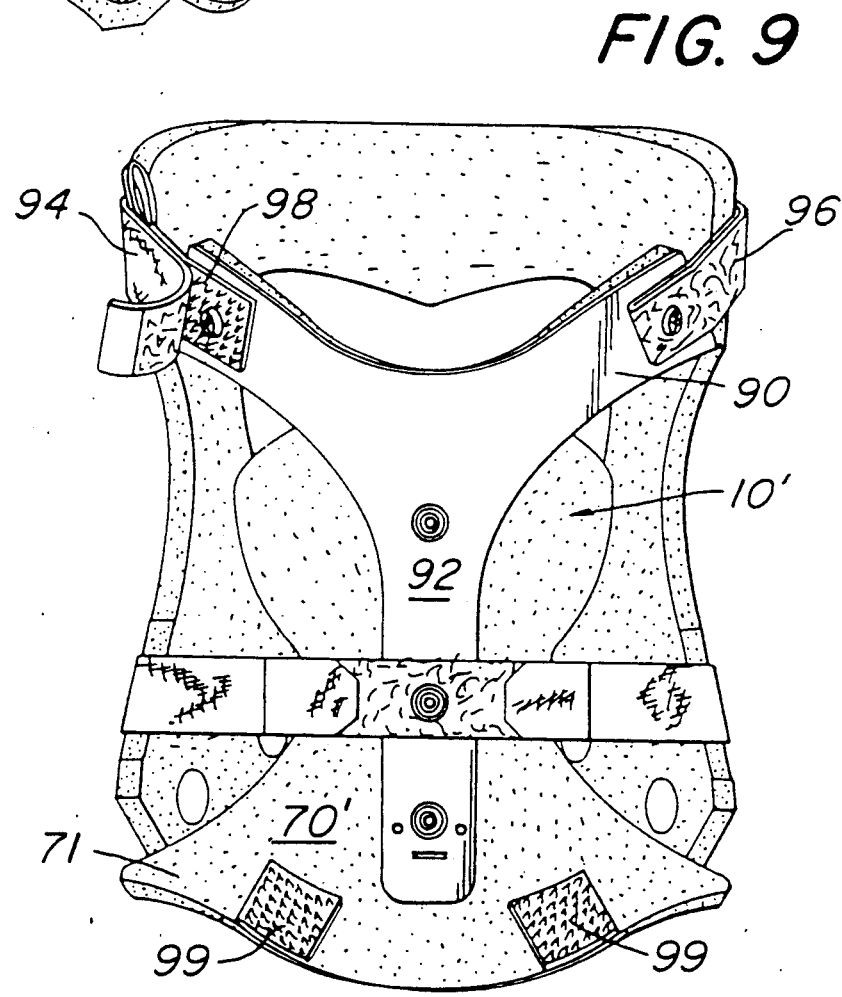
FIG. 9 is a rear elevational view of the third alternate embodiment illustrated in FIG. 8.

In FIG. 9, the head immobilizer 10' is illustrated. The head rest 90 is generally the same as the head rest discussed above, but it is integral with the rear collar's reinforcement member 92. A strap, or "halo" strap 94 is affixed to the free end of one arm of the head rest 90 and has a length which is sufficient to encircle the mask 18 and victim's forehead and overlaps the other arm. Strap 94 includes VELCRO ® loops 96 which engage VELCRO ® hooks 98 which are affixed to the other arm of head rest 90, however the other strap configurations discussed above can be used instead. With regard to the other strap configurations (FIGS. 4 and 5), patches of VELCRO ® 99 are affixed to the lower edge of rear collar half and are provided so that straps from the head rest may be affixed thereto without interference with collar half securing straps.

The skirt 71 of the rear collar half 70 is enlarged to contact a greater portion of the victim's shoulder thereby impeding side-to-side head tilt.

Figure 10:
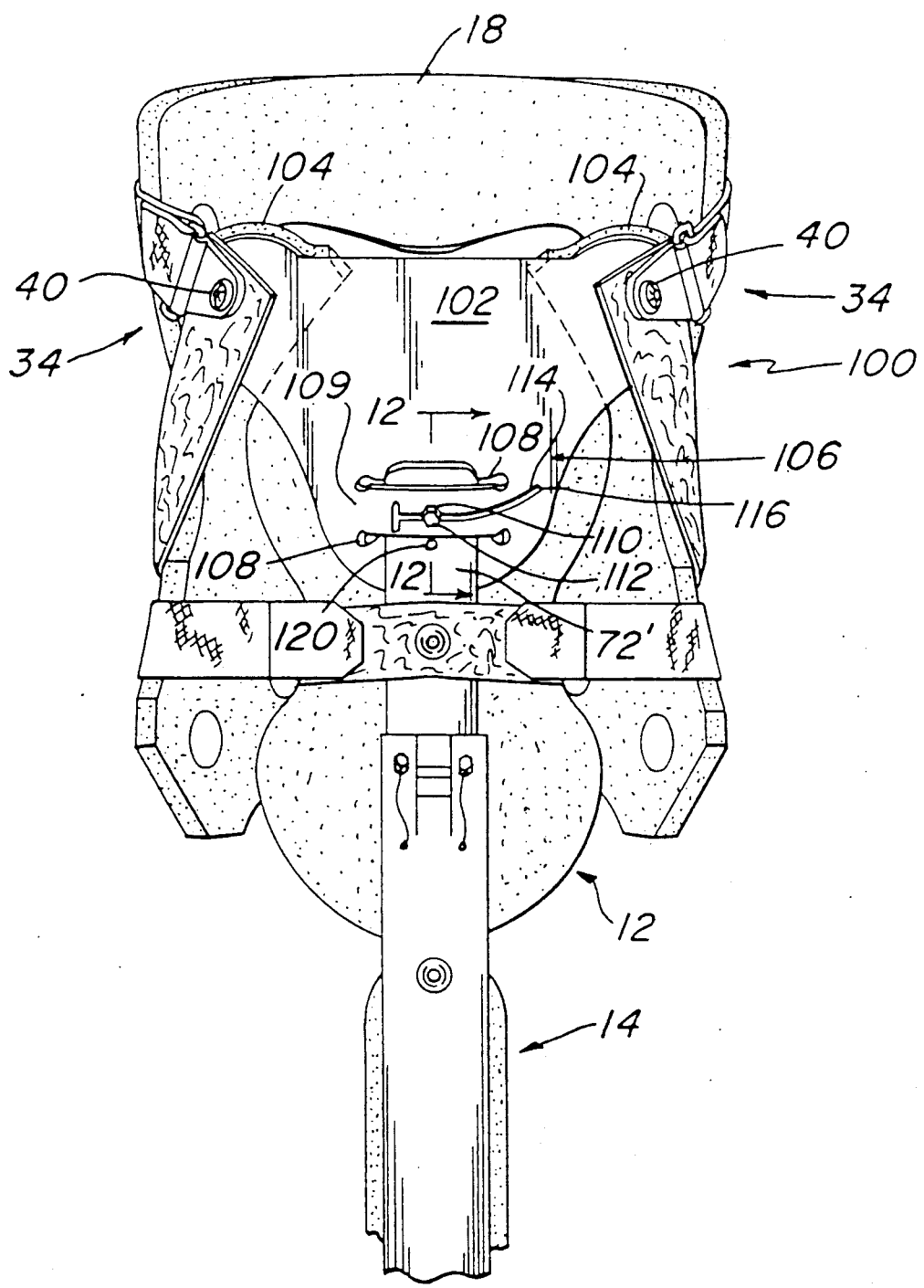
FIG. 10 is a rear elevational view of a fourth alternate embodiment of the present invention.

In FIG. 10, a head immobilizer 100 is illustrated. Immobilizer 100 is the same as the immobilizer illustrated in FIG. 3 except as noted below. A die cut, generally triangular, semi rigid plastic member 102 replaces the "T" shaped member 16 of FIG. 3. Member 102 is much more economical to produce than member 16.

The plastic material used to make member 102 may be nylon, but other material which can be die cut and are semi rigid may be used. Cushion members 104 are located in the uppermost corners of member 102 and are engageable with the victim's head. Cushion members 102 perform a two fold function: first, they rest against the victim's head to lessen any discomfort; second, they serve as anchors for the fasteners to which seals fastening device 34 on member 102. Members 102 are preferred, but not required.

Member 102 is releasably attached to a reinforcement member 72' as follows. A sleeve attachment device 106 is located in the lower most corner of member 102. Device 106 comprises two horizontal and parallel slits 108 which have a length greater than the width of the reinforcement member 72' and define band 109 therebetween. An enlarged circular opening is located at the end of each slit. The slits are sufficient wide so that the reinforcement member 72' may pass there-through. See FIG. 12. A hole 100 is located between slits 108 in band 109 and is sized to receive a pin or rivet 112. A wire fastener or nylon fastener 114 secures pin to member 102 and is anchored to member 102 through hole 116 and to pin 112 through hole 110.

Reinforcement member 72' is the same as illustrated in FIG. 3 except as follows. A stop 120 comprises a boss or plastic bar stop which is provided on member 72'. A hole 122, through member 72', is sized for receipt of pin 112. When strap 109 of member 102 is slid over member 72', stop 120 prevents further downward travel of member 102 and aligns holes 110 and 122. Pin 112, preferably the same ass illustrated in FIG. 4 of U.S. Pat. No. 4,515,153 which is incorporated herein by reference, is then snapped into the aligned holes and secures member 102 to member 72'.

Figure 11:
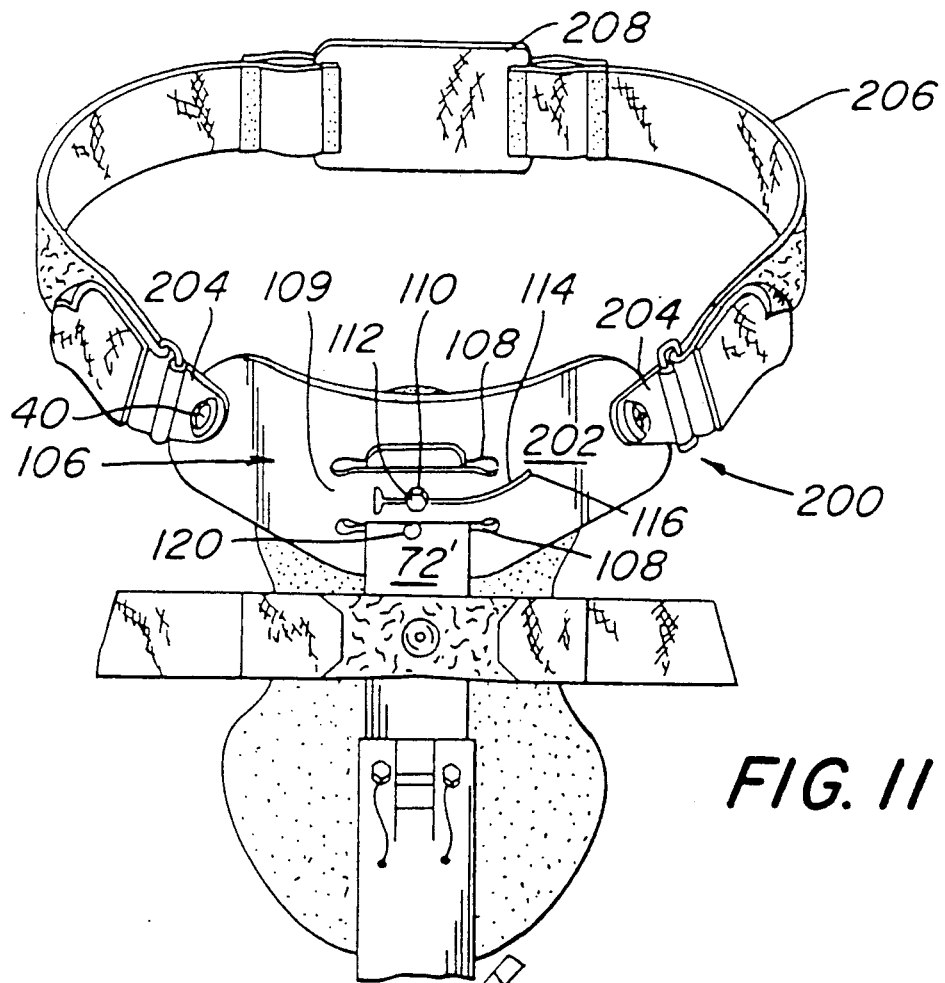
FIG. 11 is a rear elevational view of a fifth alternate embodiment.

In FIG. 11, a head immobilizer 200 is illustrated and is similar to the embodiments of FIGS. 6 and 7 in that it does not utilize the mask 16. A member 202 is releasably attachable to reinforcement member 72' in the same manner, i.e. via device 106, as described above with regard to the embodiment of FIGS. 10 and 12. Buckles 204 are secured, e.g. rivets 40, to the lateral ends of member 202. A strap 206, comprising VELCRO ® fastening members at its terminal, has a "VEL-STRETCH" member 208 secured, in a convention manner, between its ends. "VEL-STRETCH" is an elastomeric version of VELCRO ® and is provided to allow strap 206 to stretch due to swelling of the victim's head.

Figure 12:
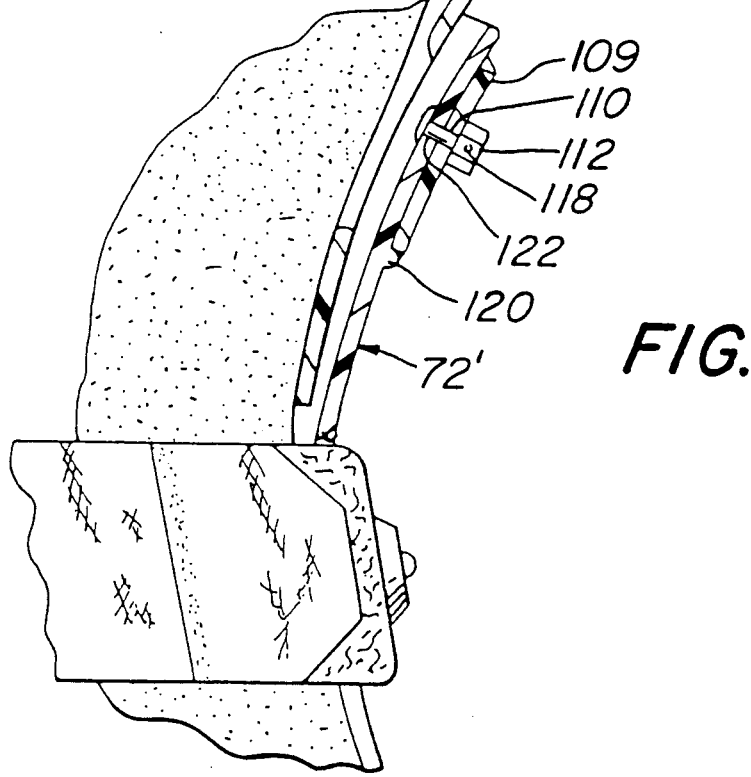
FIG. 12 is a sectional view of the fourth alternate embodiment taken along sectional line 12—12 of FIG. 10.

Referring to FIGS. 13-16, an alternate embodiment 250 of the sleeve attachment device 106 illustrated in FIGS. 10-12 is shown. Sleeve attachment device 250 allows the extremely quick and easy attachment of and removal of member 252 from the reinforcement member 254. Generally, member 252 and reinforcement member 254 are the same as previously described members 102 and 202 and reinforcement members 72 and 72', except as noted below. Moreover, device 250 can be readily adapted for use with any of the releasably attachment mechanisms discussed hereinabove or with other apparatus requiring a means for extremely quick and easy attachment of and removal of one member from another.

Sleeve attachment device 250 is extremely valuable with regard to emergency medical situations. That is in any situation where time and simplicity of operation can means the difference between life and death, device 250 provides the necessary features as will be apparent from the discussion below.

In emergency medical situations, which often arise in a dark or cold or otherwise hostile environment, small components requiring precise alignment are typically not preferred.

Member 252 is provided with slots 108 that form a band 109, previously described, but is not provided with hole 110, pin 112, fastener 114 or hole 116. Although the eliminated components perform their intended function well, because of their size and the movements necessary to implement their function, they are not preferred in emergency medical situations. Member 252, which is made of a flexible but semi-rigid material such as plastic, should be provided with finger grip surfaces, such as tabs 256. Although tabs 256 are preferred, they are optional. Additionally the grip surfaces should preferably be rough or provided with ribs, or knurled, or otherwise adapted to ensure good frictional contact between the fingers and the member. The movement of member 252 will be discussed below.

Reinforcement member 254 is provided with a lower stop 258 and an upper boss 260. Stop 258 and boss 260 are parallel to one another, are spaced apart a distance sufficient for the receipt of band 109, and are located proximal the uppermost end of the member 254.

Stop 258 preferably has a planar face 262 which is abutted by band 109 and which is preferably oriented to member 254 at a right angle, however, an acute angle could be used. The height of the planar face 262, as measured from member 254 to the outermost or uppermost point on stop 258, should be greater than the thickness of band 109 and of a sufficient height to prevent band 109 from riding or jumping over stop 258.

Boss 260 is provided with a first surface 264 and a second surface 266. The height of boss 260, as measured from member 254 to the outermost or uppermost point on boss 260, is preferably equal to the thickness of band 109; however, a lower height would be allowable if it is great enough to ensure against accidental or inadvertent passage of band 109 thereover and a higher height would be allowable if it is not so great as to impede the passage of band 109 thereover.

The first surface 264 is slanted; the leading or lowermost edge is located toward the terminal end of member 254 and the trailing or uppermost edge is located away from the terminal end and toward stop 258. The inclination of the slanted surface 264 is sufficient to allow band 109 to move thereacross in a quick, unimpeded and easy manner.

The second surface 266 is preferably oriented to member 254 at a right angle, however, an acute angle could be used. The function of the second surface 266 is to prevent the accidental or inadvertent release of member 252.

Sleeve attachment device 250 operates as follows: to engage or attach member 252 to member 254, preferably, tabs 256 are moved in the direction indicated by arrows 268 in FIG. 16. That movement causes band 109 to move out of alignment with the remainder of member 252 and thereby creates an opening sufficiently large so that member 254 may pass therethrough. When tabs 256 are released, member 252 returns to its "at rest" position, see FIG. 15, and band 109 is locked between stop 258 and boss 260 and member 252 is secured on member 254.

To disengage or release member 252 from member 254, the engaging operation is reversed. Namely, tabs 256 are moved in direction 268; the opening is formed; and member 254 is released.

Figure 17:
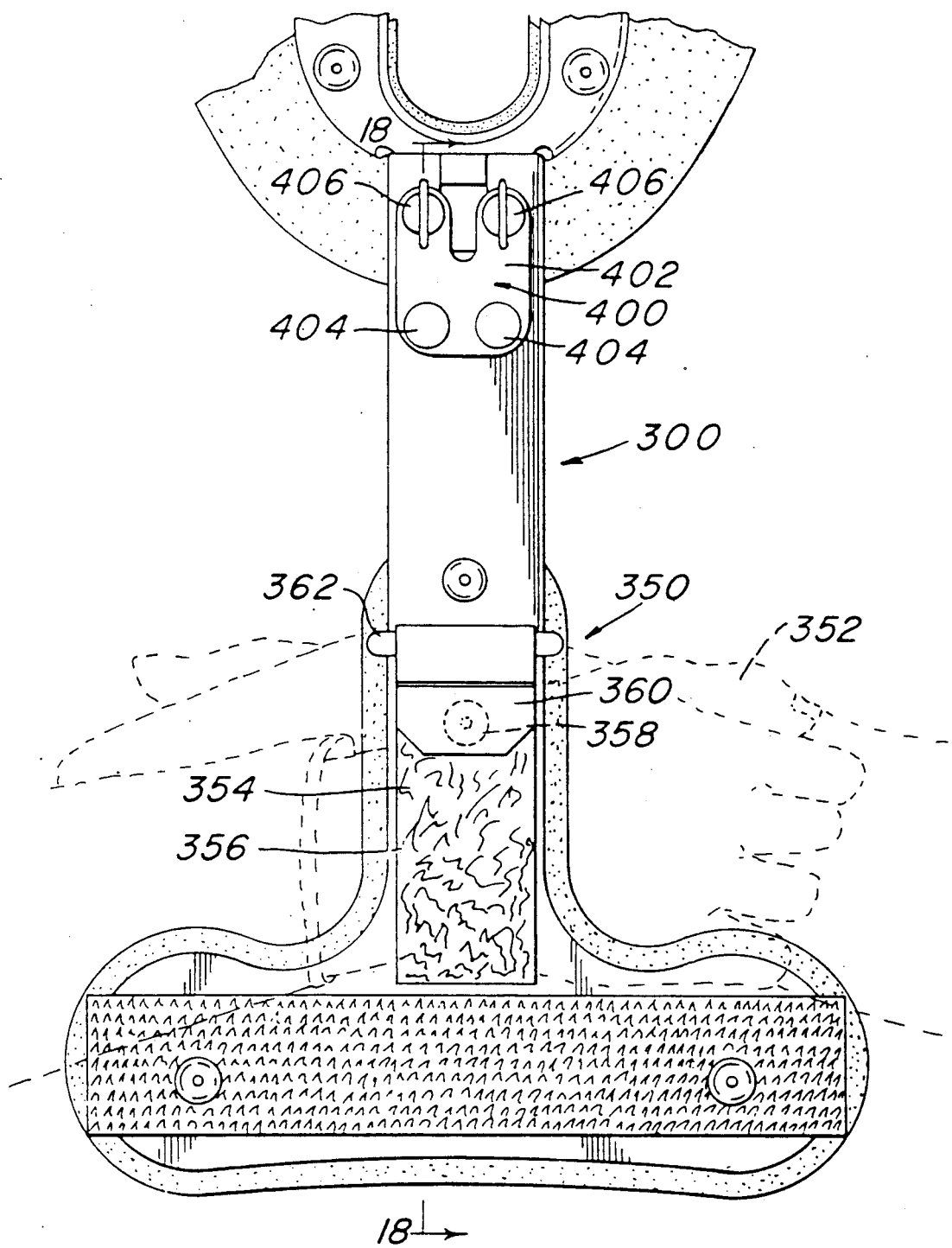
FIG. 17 is an elevational view of an alternate embodiment of the front stabilizer half illustrated in FIGS. 1, 2, 4 and 5 and of the connection device illustrated in FIGS. 1, 2, 3, 4, 5, 10 and 11.
Figure 18:
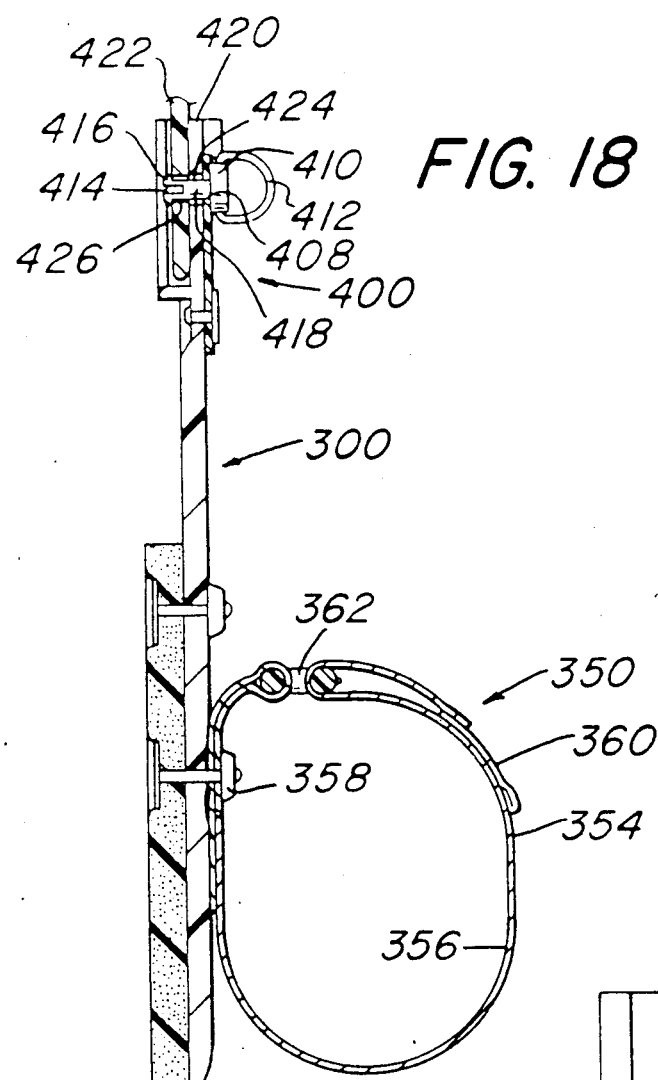
FIG. 18 is a sectional view taken along lines 18—18 of FIG. 17.
Figure 19:
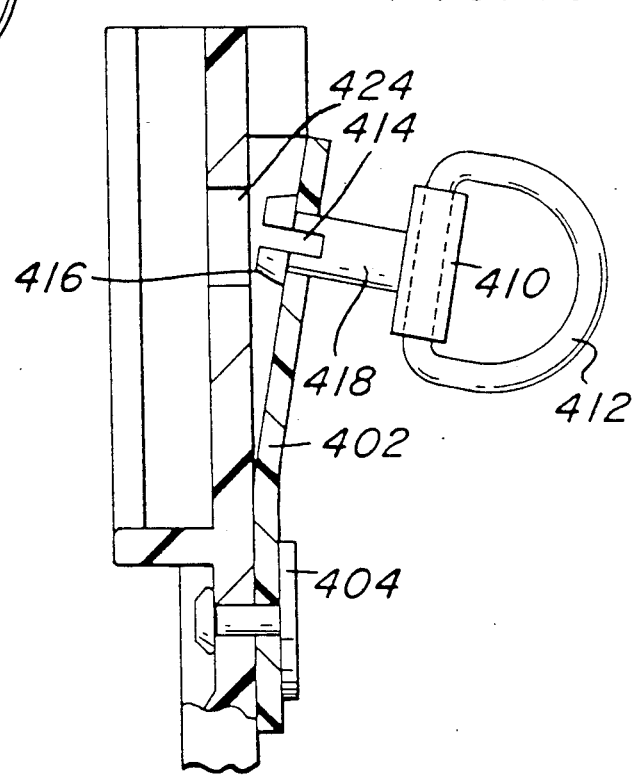
FIG. 19 is an enlarged view of an alternate embodiment of the connection device illustrated in FIGS. 1, 2, 3, 4, 5, 10 and 11 are shown in the "unlocked" position.

Referring to FIGS. 17-19, an alternate embodiment 300 of the front stabilizer half 78 and an alternate embodiment 400 of the connection device 82 are illustrated. Front stabilizer half 300 is the same as previously described but for the addition of a hands/arms securing device 350 and the substitution of the alternate connection device 400.

Hands/arms securing device 350 is particularly useful in the emergency medical situations discussed above. Often when an accident victim requires the use of the herein described collar/stabilizer combination because of trauma to the head/spine, their hands/arms 352 dangle from the body and need to be secured during movement of the victim. The hands/arms 352 placement is typically across the victim's chest; device 350 provides a simple, convenient way of securing the hands/arms across the victim's chest. Preferably, device 350 comprises a VELCRO ® strap 354 which is affixed to half 300 and of sufficient weight to completely surround and securely hold both wrists of the victim. Strap 354 has a loop portion 356 which is affixed to half 300 via any conventional manner such as a rivet 358 and which forms a major portion of the strap 354 and has a hook portion 360 which is secured to the free or terminal end of strap 354 away from rivet 358 and which is adapted to be secured to loop portion 356. Additionally, a buckle 362 is secured on the strap 354 adjacent the rivet 358 and is adapted engage the free end of the strap before it is secured to itself. See FIG. 18.

Connection device 400, illustrated in use on the front stabilizer half, but which can be used on the rear stabilizer half as well, is utilized on a collar/stabilizer combination for use in emergency medical situations. As discussed above, small components requiring precise alignment are not preferred in emergency medical situations. The connecting device 400 overcomes the special problems of the emergency medical situations by utilizing larger, self-aligning components. Connection device 400 comprises a resilient member 402 which is affixed to the reinforcement member in any conventional manner, such as rivets 404. The resilient number 402 is preferably U-shaped. See FIG. 17. At the unaffixed end of member 402, a pin or rivet 406 is permanently secured thereto via a hole 408. The pin 406 may slide within hole 408 but is not removable therefrom. Preferably, two pins 406 are used. See FIG. 17. Each pin 406 includes an outer end having a large head 410 with a large ring 412 therethrough and an inner end having a slot 414 therethrough with a beveled flange 416 therearound. The outer end is accessible to emergency medical personnel and the inner end is releasably engagable with a portion of the collar. The outer and inner ends are connected by a shaft 418 that has a sufficient length to span member 402, the reenforcement member 420 and the portion 422 of the collar. See FIG. 18. The reinforcement member 420 and collar portion 422 have holes 424 and 426 respectively, that are aligned when the collar portion is completely inserted into the reinforcement member. The hole 408 of member 402 is permanently aligned with hole 424 of reinforcement member 420.

In operation, the reinforcement member 420 is slid onto collar portion 422 until the members abut whereby holes 424 and 426 are aligned. Pin 406, in the unlocked position (see FIG. 19), is pressed into locking engagement with collar portion 422 and through reenforcement member 420 (see FIG. 18). To remove pin 406 from the locked position, ring 412 is gripped and yanked or pulled out from the collar portion and reinforcement member.

Figure 20:
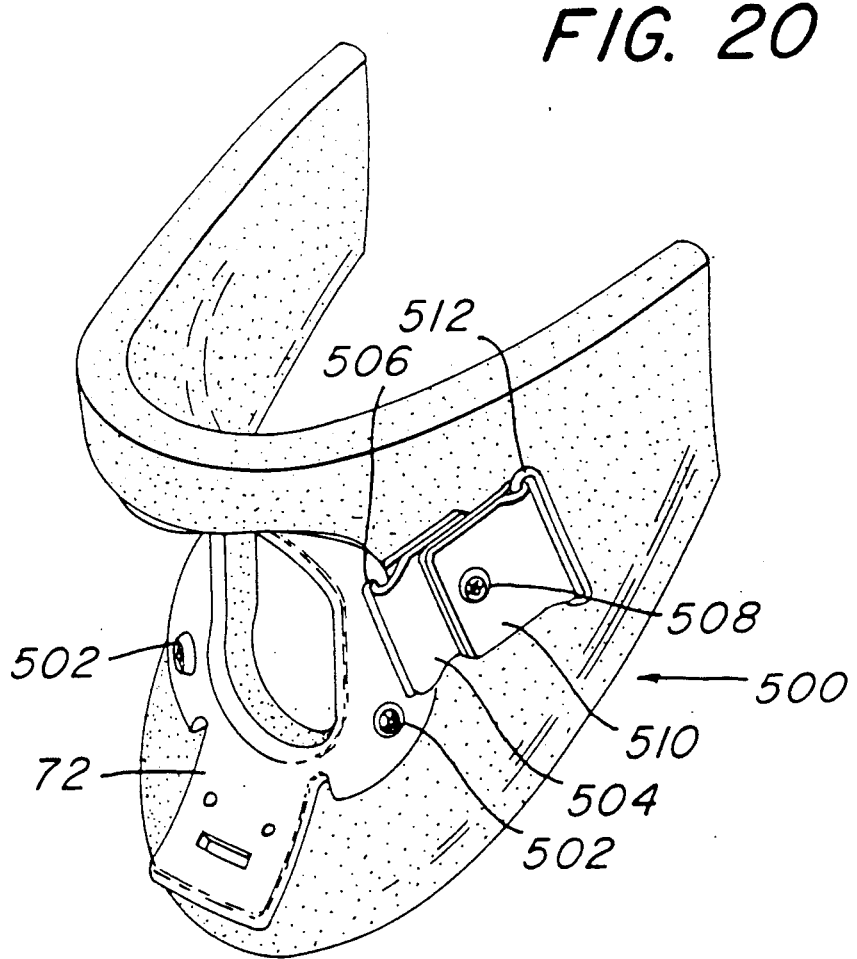
FIG. 20 is an isometric view of an embodiment of the front collar half.

Referring to FIG. 20, an alternate embodiment of the front collar half 500 is illustrated. The half 500 is substantially the same as described above. The half 500 is illustrated with the trachea opening but it is optional. The lower portion of reenforcement member 72 is fastened to the collar half 500 preferably by rivets 502. The upper portion of member 72 is held against the collar half 500 by strap 504 (only one shown). Strap 504 is made of any strong material and is looped through slot 506 of member 72. A rivet 508 fastens the strap 504 to the collar half 500. A second strap 510 is also fastened to the collar half 500 via rivet 508. Second strap 510 has a buckle 512 attached thereto. Second strap 510 is pivotable about rivet 508. The buckle 512 is for engagement with a VELCRO ® strap affixed to the rear collar half. When the straps are passed through the buckles and pulled taut so as to fasten the collar about the victim's neck, the buckle pivots and thereby allows the front half 500 to move into alignment with the victim's chin. In other words, the pivotable buckle performs a dual function; first it allows the front half to be pulled back and into engagement with the victim and second it allows the front half to pivot and aligns with the victim's chin.

Referring to FIG. 1, a swatch 55 of a VELCRO ® material is affixed to the portion of mask 54 which overlaps the forehead of the victim. The swatch 55 is for engagement with a strap (not shown) from a spine board (not shown). Spine boards with strap are known and often used in emergency medical situation to move the victim. The straps are secured around the victim to secure the victim to the board. If a VELCRO ® strap is substituted for a conventional (non-VELCRO ® strap and the VELCRO ® strap is located on the board adjacent the victim's head, then it can be fastened to the swatch 55 and further secure the victim's head to the board.

The present invention may be embodied in other specific forms without departing from the spirit or essential attributes thereof and, accordingly, reference essential attributes thereof and, accordingly, reference should be made to the appended claims, rather than to the foregoing specification, as indicating the scope of the invention.

We claim:

1. A head immobilizer for use with a cervical collar adapted for application to a victim's neck at least substantially encircling the neck between the victim's head and torso to substantially immobilize the victim's neck and head, comprising:
   a head rest for supporting the rear of the victim's head above the cervical collar;
   means adapted for releasably coupling said head rest to said cervical collar such that said head rest and cervical collar are rigidly secured together;
   a unitary mask means for encircling the front of the victim's face having an opening therethrough for substantially exposing said victim's face while securing said victim's head to said head rest;
   means for connecting said mask means to said head rest, such that at least one portion of said mask means is adapted to overlap the victim's forehead and another portion of said mask means is adapted to overlap a front end of said cervical collar beneath the victim's face;
   whereby a victim's head is immobilized between said head rest, mask means, and cervical collar.

2. The head immobilizer according to claim 1 wherein said connecting means comprises:
   means for fastening being affixed to said head rest;
   means for mating being affixed to said mask means and for engaging said fastening means; and
   means for securing affixed to said mask means and for engaging said fastening means.

3. The head immobilizer according to claim 1 wherein said connecting means includes means for connecting said mask means to said head rest and said collar.

4. The head immobilizer according to claim 1 wherein said head rest comprises a reinforcement member and a padding material affixed thereto.

5. The head immobilizer according to claim 1 wherein the cervical collar includes a vertical, reinforcing member and wherein said means for coupling comprises a stem on said head rest provided with a channel adapted for receiving said vertical reinforcing member.

6. The head immobilizer according to claim 1 wherein said mask means comprises a resilient foam material.

7. The head immobilizer according to claim 1 wherein said mask means comprises a pair of downwardly extending wings which contact said victim's clavicle.

8. The head immobilizer according to claim 7 wherein each of said wings comprises a reinforcement member affixed thereon.

9. The head immobilizer according to claim 1 wherein said head rest comprises a semi-rigid plastic member.

10. The head immobilizer according to claim 1 wherein said coupling means comprises sleeve means adapted for sliding over an upright reinforcement member located on a rear portion of said cervical collar.

11. The head immobilizer of claim 1 in combination with said cervical collar.

12. A head immobilizer for use in combination with a cervical collar, said cervical collar comprising a front and a rear half, each said half being U-shaped, the front and rear halves being adapted to be applied to a victim's neck at least substantially encircling the neck between the victim's head and torso to substantially immobilize the victim's neck and head, and said rear half including a reinforcing member, said immobilizer comprising:
   a head rest being T-shaped and having a stem and two arms, a distal end on each said arm, said stem being adapted to releasably engage said reinforcing member of said rear collar half to rigidly secure said head rest and said reinforcing member together;
   fastening means affixed to said distal ends of each said arm;
   a unitary mask means for encircling the front of the victim's face having an opening therethrough for substantially exposing the victim's face while securing said victim's head to the head rest;
   mating means affixed to said mask means for engaging said fastening means; and
   securing means affixed to said mask mask for engaging said fastening means;
   at least a portion of said mask means being adapted for overlapping said front collar half front beneath the victim's face when said mating means and said securing means engage said fastening means, whereby said victim's head is immobilized between said head rest, mask means, and cervical collar, when said fastening means is engaged with said mating means and said securing means.

13. The head immobilizer according to claim 12, wherein said fastening means further comprises buckle means and strap means.

14. The head immobilizer according to claim 12, wherein said mating means further comprises strap means.

15. The head immobilizer according to claim 12, wherein said securing means further comprises buckle means.

16. The head immobilizer according to claim 12, wherein said head rest further comprises a reinforcement member and a padding material affixed to said member.

17. The head immobilizer according to claim 12, wherein said stem defines a channel sized for receipt of the reinforcing member of said rear half.

18. The head immobilizer according to claim 12, wherein said mask means further comprises a resilient foam material.

19. The head immobilizer according to claim 12, wherein said mask means further comprises a wing which extends away from a remainder of said mask means at an angle, and which spans a space between said victim's jaw and clavicle.

20. The head immobilizer according to claim 19, wherein said wing further comprises a reinforcement member affixed thereto.

21. The head immobilizer according to claim 12, wherein said rear collar half further comprises a fastening affixed thereto for engagement by said fastener means.

22. The head immobilizer of claim 12 in combination with said cervical collar said reinforcing member releasably, interfittingly matingly engaging with said head rest forming a substantially rigid integral structure.

23. A head immobilizer for use in combination with a cervical collar, said cervical collar comprising a front and a rear half, each said half being U-shaped, said halves being adapted to at least substantially encircle the victim's neck between the victim's head and torso when the halves are applied opposingly to the victim's neck to substantially immobilize said neck and head, said rear collar half including a reinforcing member, said head immobilizer comprising:
a head rest being T-shaped and having a stem and two arms, a distal end on each said arm, said stem being adapted to releasably engage said reinforcing member of said rear half to rigidly secure said head rest and said reinforcing member together;
fastening means affixed to said distal ends of each said arm and including strap means and buckle means;
unitary mask means for encircling the front of the victim's face having an opening therethrough for substantially exposing a victim's face while securing said victim's head to said head rest and having a wing which extends away from a remaining portion of said mask means at an angle and which spans a space between the victim's jaw and clavicle;
mating means affixed to said mask means for engaging said fastening means, said mating means including strap means;
securing means affixed to said mask means for engaging said fastening means, said securing means including buckle means;
a portion of said mask means adjoining said wing overlapping, in part, a front side of said front cervical collar half beneath the victim's face when said fastener means is connected with said mating means and said securing means, whereby the victim's head is immobilized between said head rest, mask means, and cervical collar, when said fastening means is connected with said mating means and said securing means.

24. The head immobilizer of claim 23 in combination with said cervical collar said reinforcing member releasably, interfittingly matingly engaging with said stem forming a substantially rigid integral structure.

25. A head immobilizer for use with a cervical collar comprising:
a head rest for supporting the rear of a victim's head, said head rest being integral with said cervical collar;
a unitary mask for encircling the front of the victim's face having an opening therethrough for substantially exposing said victim's face while securing said victim's head to said head rest;
means for connecting said mask to said head rest, such that one portion of said mask overlaps a victim's forehead and another portion of said mask overlaps said collar;
whereby a victim's head is immobilized between said head rest, mask, and collar.

26. An emergency medical system for immobilizing a victim's neck, head and/or spine comprises:
a collar including a front half and a rear half which together encircle said victim's neck, means for reinforcing each said half, said reinforcement means being attached to each said half, means for interconnecting each said half to one another;
means for head immobilization being releasably attachable to said collar, said head immobilization means including a head rest and means for securing said victim's head to said head rest, said head rest being releasably attachable to said collar, and said securing means being operatively associated with said head rest;
a unitary mask means with an opening therethrough for substantially exposing said victim's face while encircling said victim's face and securing said victim's head to said head rest, and
stabilizer means for stabilizing including a front member and a rear member, said member being releasably attachable to said collar separately and independently of said head immobilization means, and means for interconnecting said front member and said rear member.

27. The system according to claim 26 wherein said collar includes a tracheotomy hole in said front half.

28. The system according to claim 26 wherein said head rest releasably interconnects with a rear reinforcement member of said collar, said head rest being made of flexible material and including a pair of parallel slits defining a band, said rear reinforcement member of said collar being made of a rigid material and including stop means and boss means, said band and a remainder of said head rest defining an opening when said head rest is moved to a flexed position, said opening being sufficiently large for receipt of said rear reinforcement member, sand said head rest being locked on said rear reinforcement member when said head rest is released and said head rest is at a rest position.

29. The system according to claim 26 wherein said stabilizer means comprises means for connecting said stabilizer means to said collar, said connecting means including a resilient member having a first end and a second end, said second end being affixed to said stabilizer means and said first end being movable between a locked and an unlocked position, pin means for releasable engagement and self alignment with said collar and being affixed to said first end of said resilient member, whereby said pin means is pressed into locking engagement with said collar and is pulled out of locking engagement with said collar.

30. The system according to claim 26 wherein said stabilizer further comprises means for securing said victim's hands/arms including strap means having sufficient length to encircle two wrists of said victim, being affixed to the stabilizer and for immobilizing the hands/arms of said victim.

31. A cervical collar to be applied to the neck of a person for supporting the person's head comprising:
   front and rear discrete body halves, each body half being U-shaped and preformed from a soft, flexible, foam material, adjustable strap means having a portion coupled with each of said halves for releasably interconnecting free ends of said halves in overlapping relation;
   a first rigid support means located at least in a central portion of the U-shaped front half and fixed with the front half for supporting a front portion of the person's head;
   a second rigid support means located at least in a central portion of the rear half and fixed with the rear half for supporting a rear portion of the person's head, the second rigid support means including a rigid head rest portion extending up-wardly above the adjustable strap means;
   a unitary flexible head restraining device having a central opening to be applied to a person's face encircling the face while exposing the face through the opening; and
   releasable connection means for releasably connecting the flexible head restraining device with the rigid head rest portion.

32. The cervical collar of claim 31 wherein the second rigid support means includes a rigid support member fixed with the rear body half and a separate head rest, the head rest including a stem portion removably coupled to the rigid support member and a pair of arms extending transversely from the stem portion, and wherein the releasable connection means couples the flexible head restraining device with each of the pair of arms.

33. The cervical collar of claim 32 further comprising first stabilizer coupling means on a lower end of the first rigid support member and second stabilizer coupling means on a lower end of the second rigid support member for removably coupling to the first and second rigid support members with a stabilizer securable below the cervical collar to the torso of the person wearing the cervical collar.

* * * * *